(12) United States Patent
Ravikumar et al.

(10) Patent No.: US 7,195,592 B2
(45) Date of Patent: Mar. 27, 2007

(54) SURGICAL RETRACTOR APPARATUS FOR USE WITH A SURGICAL PORT

(76) Inventors: Sundaram Ravikumar, 265 Hardscrabble Rd., Briarcliff Manor, NY (US) 10510; John Rutkowski, 8 Knoll Dr., Jackson, NJ (US) 08527

( * ) Notice: Subject to any disclaimer, the term of this patent is extended or adjusted under 35 U.S.C. 154(b) by 424 days.

(21) Appl. No.: 10/766,597

(22) Filed: Jan. 27, 2004

(65) Prior Publication Data
US 2005/0165281 A1 Jul. 28, 2005

(51) Int. Cl.
*A61B 1/32* (2006.01)
(52) U.S. Cl. .................................... 600/219; 600/224
(58) Field of Classification Search ............... 600/208, 600/214, 215, 219, 224, 231, 233, 234, 204
See application file for complete search history.

(56) References Cited

U.S. PATENT DOCUMENTS

| | | | |
|---|---|---|---|
| 2,548,602 A | 4/1951 | Greenburg | 128/4 |
| 3,044,461 A | 7/1962 | Murdock | 128/4 |
| 4,424,724 A | 1/1984 | Bookwalter et al. | 74/540 |
| 4,716,901 A | 1/1988 | Jackson et al. | 128/343 |
| 4,899,729 A | 2/1990 | Gill et al. | 128/3 |
| 5,052,373 A | 10/1991 | Michelson | |
| 5,176,659 A | 1/1993 | Mancini | |
| 5,183,464 A | 2/1993 | Dubrul et al. | 128/3 |
| 5,197,971 A | 3/1993 | Bonutti | 606/192 |
| 5,232,451 A | 8/1993 | Freitas et al. | 606/174 |
| 5,312,360 A | 5/1994 | Behl | |
| 5,370,134 A | 12/1994 | Chin et al. | 128/898 |
| 5,431,676 A | 7/1995 | Dubrul et al. | 606/185 |
| 5,441,486 A | 8/1995 | Yoon | |
| 5,460,170 A | 10/1995 | Hammerslag | 600/201 |
| 5,503,617 A | 4/1996 | Jako | |
| 5,520,610 A | 5/1996 | Giglio et al. | |
| 5,667,481 A | 9/1997 | Villalta et al. | |
| 5,674,240 A | 10/1997 | Bonutti et al. | 606/198 |
| 5,688,223 A | 11/1997 | Rosendahl | 600/215 |
| 5,728,046 A | 3/1998 | Mayer et al. | |
| 5,795,289 A | 8/1998 | Wyttenbach | 600/207 |
| 5,813,978 A | 9/1998 | Jako | |
| 5,827,319 A | 10/1998 | Carlson et al. | 606/191 |
| 5,928,139 A | 7/1999 | Koros et al. | |
| 5,944,658 A | 8/1999 | Koros et al. | |
| 5,957,902 A | 9/1999 | Teves | |
| 5,967,891 A | 10/1999 | Riley et al. | 454/154 |
| 5,967,970 A | 10/1999 | Cowan et al. | |
| 5,967,972 A | 10/1999 | Santilli et al. | 600/232 |
| 6,080,174 A | 6/2000 | Dubrul et al. | 606/185 |
| 6,083,154 A | 7/2000 | Liu et al. | |
| 6,159,179 A | 12/2000 | Simonson | |
| 6,224,608 B1 | 5/2001 | Ciccolella et al. | |

(Continued)

*Primary Examiner*—Cary E. O'Connor
(74) *Attorney, Agent, or Firm*—Gordon & Jacobson, PC (57) ABSTRACT

An improved surgical retraction apparatus (and corresponding method of operation) includes a plurality of rigid retraction members disposed about a central axis that move radially with respect to the central axis between a closed state and an open state. In the closed state, the retraction members form a central opening that is adapted to closely fit around the tubular section of a surgical port device. In the illustrative embodiments, a planetary gear train, cable assemblies and lever arms may be used to control radial movement of the retraction members with respect to the central axis.

27 Claims, 8 Drawing Sheets

U.S. PATENT DOCUMENTS

| | | |
|---|---|---|
| 6,228,068 B1 | 5/2001 | Yoon |
| 6,245,052 B1 | 6/2001 | Orth et al. .................. 604/506 |
| 6,277,094 B1 | 8/2001 | Schendel |
| 6,325,812 B1 | 12/2001 | Dubrul et al. .............. 606/185 |
| 6,358,266 B1 | 3/2002 | Bonutti ...................... 606/190 |
| 6,440,063 B1 | 8/2002 | Beane et al. ................ 600/207 |
| 6,464,634 B1 | 10/2002 | Fraser |
| 6,616,678 B2 | 9/2003 | Nishtala et al. ............. 606/198 |
| 6,626,859 B2 | 9/2003 | Von Segesser ............... 604/28 |
| 6,706,017 B1 | 3/2004 | Dulguerov |
| 6,712,795 B1 | 3/2004 | Cohen |
| 2004/0087833 A1 | 5/2004 | Bauer et al. |
| 2005/0159650 A1 | 7/2005 | Raymond et al. |

SURGICAL RETRACTOR APPARATUS FOR USE WITH A SURGICAL PORT

BACKGROUND OF THE INVENTION

1. Field of the Invention

This invention relates broadly to surgical instruments. More particularly, this invention relates to a retraction apparatus for use with a surgical port device. In addition, the invention relates to an improved methodology for performing retraction of the tissue surrounding a surgical port device.

2. State of the Art

Laparoscopic (Thoracoscopic) surgical procedures are facilitated by the use of surgical ports (commonly referred to as "trocars") that provide access into the abdominal cavity (thoracic cavity). Various surgical instruments (e.g., imaging probes, cutting blades, clamps/suturing devices, etc.) are inserted into the abdominal cavity (thoracic cavity) via such ports and are manipulated in the cavity. Typically, such surgical ports employ a cannula as the passageway for the various instruments. Often, internal pressures in the body cavity are elevated by insufflation via an external pressure source operably coupled to the body cavity through an inlet in the surgical port. In such configurations, the surgical ports often employ gaskets disposed upstream from the inlet that maintain the elevated internal pressures in the body cavity while inserting/removing instruments through the cannula of the port.

In many laparoscopic/thoracoscopic surgical procedures, it is desirable at some point in the procedure to provide the surgeon with a relatively large size opening into the body. The large size opening enables the surgeon to use larger surgical instruments. It also enables visualization of the surgical site without a camera. Finally, the large size opening enables the removal of larger organs (or pieces of such large organs) through the body wall in less time.

Various surgical retractors have been developed to assist surgeons in retracting tissue surrounding an incision into the body wall. One common configuration for surgical retractors is to mount a plurality of retractors to a circular support ring. An example of such a configuration is shown in U.S. Pat. No. 5,688,223. However, this configuration is unsuitable for use with a surgical port device because its nested configuration (when closed) will not fit around a surgical port device. Moreover, the radial position of the arms of the retractor are manually adjusted individually, which is cumbersome and time-consuming.

Thus, there remains a need in the art for improved surgical retraction devices that are suitable for use with surgical ports and thus overcome the limitations provided by these prior art retraction devices.

SUMMARY OF THE INVENTION

It is therefore an object of the invention to provide a surgical retraction device (and corresponding method of operation) that is suitable for use with a surgical port device.

It is another object of the invention to provide a surgical retraction device (and corresponding method of operation) that quickly and effectively forms an opening of variable size through a body wall.

It is a further object of the invention to provide a surgical retraction device wherein the user can easily adjust the size of the opening through the body wall.

It is also an object of the invention to provide a surgical retraction device suitable for use in a broad range of laparoscopic and thoracoscopic surgical procedures.

In accord with these objects, which will be discussed in detail below, an improved surgical retraction apparatus is provided. The apparatus has a plurality of rigid retraction members disposed about a central axis that move radially with respect to the central axis between a closed state and an open state. In the closed state, the retraction members form a central opening that is adapted to closely fit around the tubular section of a surgical port device. In the illustrative embodiments, a planetary gear train, cable assemblies and lever arms may be used to control radial movement of the retraction members with respect to the central axis.

It will be appreciated that the radial position of the retraction members of the surgical retraction apparatus are easily adjusted to provide a wide range of opening sizes into the body, and thus are effective in retracting tissue for many different surgical applications. In addition, the surgical retraction apparatus of the present invention is simple to use and effective in conjunction with surgical port devices, and thus is effective in a wide range of laparoscopic and thoracoscopic procedures.

Additional objects and advantages of the invention will become apparent to those skilled in the art upon reference to the detailed description taken in conjunction with the provided figures.

DETAILED DESCRIPTION OF THE PREFERRED EMBODIMENTS

As used herein, the term "distal" is generally defined as in the direction of the patient and pertinent body cavity, or away from a user of the device (e.g., a doctor). Conversely, "proximal" generally means in the direction away from the patient/pertinent body cavity, or toward the user of the device.

Turning now to FIGS. 1, 2A–2C, 3A–3C, there is shown an improved surgical retraction apparatus in accordance with the present invention. The surgical retraction apparatus 10 includes a two-part housing (housing elements 12A, 12B) that supports a plurality of retraction members (for example, the five labeled 14A, 14B, 14C, 14D and 14E). The retraction members are generally L-shaped, with each having an arm (16A, 16B, 16C, 16D, 16E) that projects along a direction substantially parallel to a central axis 17 and a segment (18A, 18B, 18C, 18D, 18E) that projects radially outward from its arm. In order to the provide a bias force that maintains the arms in position against body tissue, the arms may be angled away from normal (for example, on the order of 87 degrees) as shown in FIG. 1B. The arms (16A, 16B, 16C, 16D, 16 radial direction (perpendicular to the central axis 17) by a planetary gear train. The planetary gear train includes a sun gear 22 and a plurality of planetary pinion gears 24A, 24B, 24C, 24D, 24E that mesh to the inner diameter teethed surface of the sun gear 22. The pinion gears 24A, 24B, 24C, 24D, 24E also mesh with the corresponding teethed surface 26A, 26B, 26C, 26D, 26E of the segments 18A, 18B, 18C, 18D, 18E to form a rack and pinion interface for each retraction member. A spline 20 is integral to one of the planetary gears (for example, planetary gear 24B as shown). A handle or knob (not shown) is attached to the spline 20. User rotation of the handle or knob drives the spline 20 and planetary pinion gear 24B, which acts as a drive gear to drive rotation of the sun gear 22. Pins 25A, 25B, 25C, 25D, 25E and a ring spacer 27 may be used to hold the planetary gears in place (meshed) against the inner diameter teethed surface of the sun gear 22 as shown. In this configuration, user rotation of the handle or knob in the clockwise direction causes the drive planetary pinion gear 24B to rotate in the clockwise direction, which causes the sun gear 22 to rotate in the clockwise direction. The clockwise rotation of the sun gear 22 causes the other planetary pinion gears 24A, 24C, 24D, 24E to rotate in the clockwise direction. The clockwise rotation of the pinion gears causes translation of the rack surfaces 26A, 26B, 26C, 26D, 26E in the radial direction away from the central axis. Similarly, the rotation of the or knob and drive planetary pinion gear in the counter-clockwise direction causes the sun gear 22 to rotate in the counter-clockwise direction, which causes the other planetary pinion gears 24A, 24C, 24D, 24E to rotate in the counter-clockwise direction. The counter-clockwise rotation of the planetary pinion gears causes translation of the rack surfaces 26A, 26B, 26C, 26D, 26E in the radial direction toward the central axis. In this manner, rotation of the handle or knob and drive planetary pinion gear effectuates retraction of the arms 16A, 16B, 16C, 16D, 16E in the radial direction away from (and towards) the central axis 17.

Figure 2A:
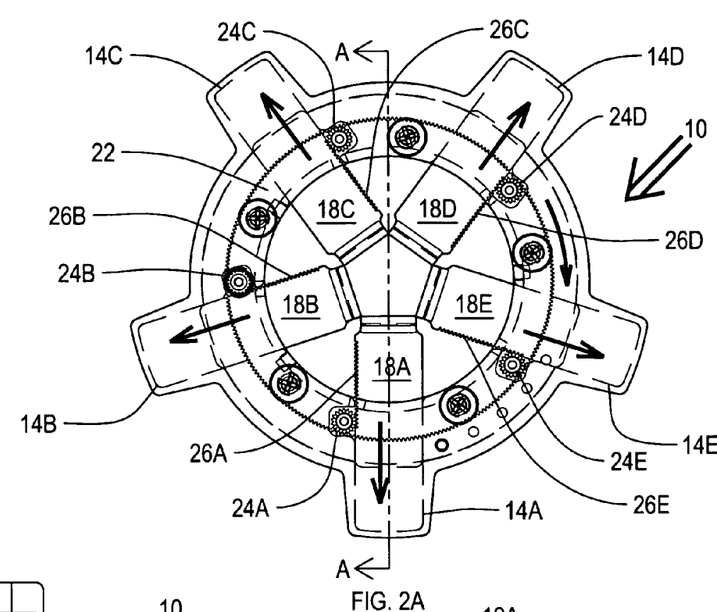
FIGS. 2A–2C illustrate the surgical retraction apparatus of FIG. 1 in its non-retracted "closed" configuration.
Figure 2B:
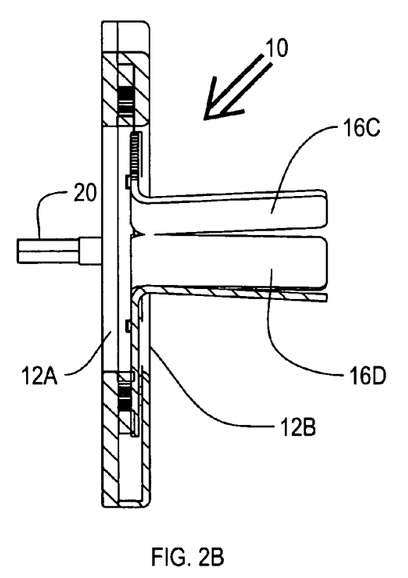
Figure 2C:
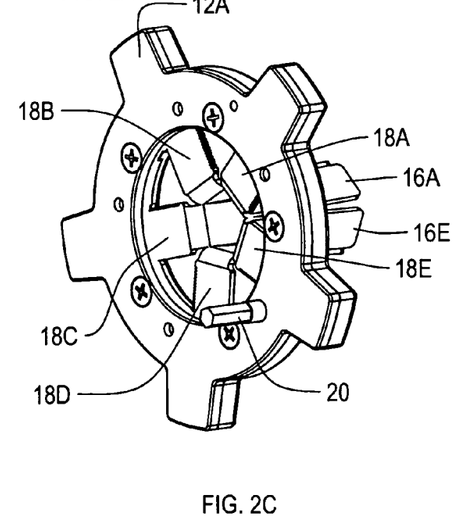

FIGS. 2A–2C illustrate the surgical retraction apparatus of FIG. 1 in its non-retracted "closed" configuration. FIG. 2B is a cross-sectional view across line A—A in FIG. 2A. In this configuration, the retraction arms 16A, 16B, 16C, 16D, 16E form a substantially-closed tube-shaped structure about the central axis 17 as best shown in FIG. 2C. Moreover, it is contemplated that the outside surfaces of the retraction arms 16A, 16B, 16C, 16D, 16E may include projections (not shown) that form a screw thread surface about the outside diameter of such tube-shape structure. The screw thread surface can be used to screw the retraction apparatus into place against the body wall and retain it in its desired position against the body wall during retraction.

Figure 3A:
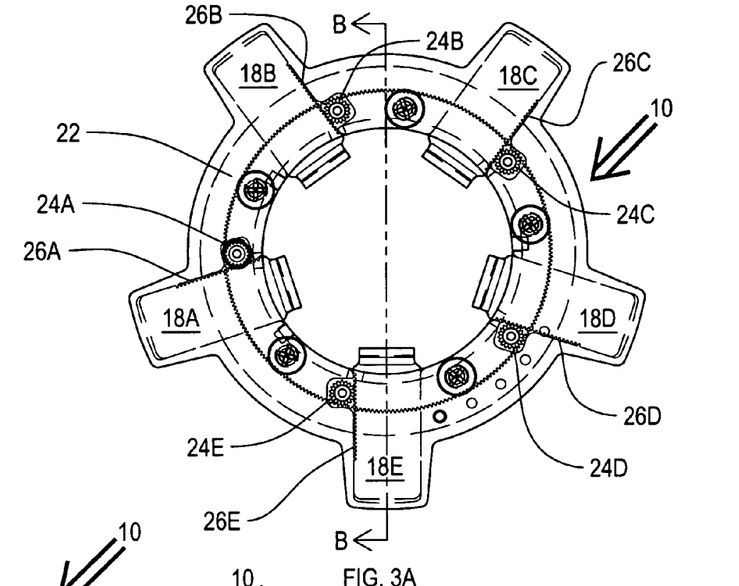
FIGS. 3A–3C illustrate the surgical retraction apparatus of FIG. 1 in its fully-retracted "open" configuration.
Figure 3B:
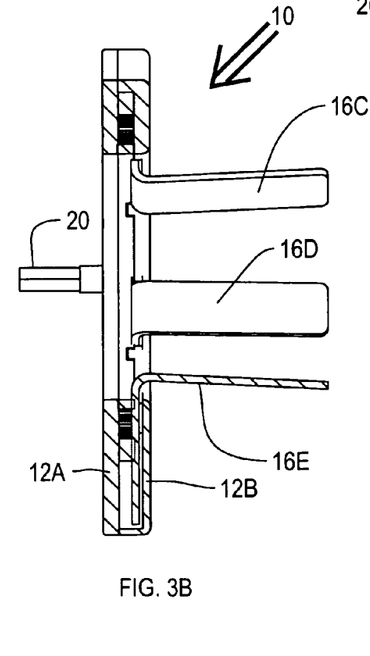
Figure 3C:
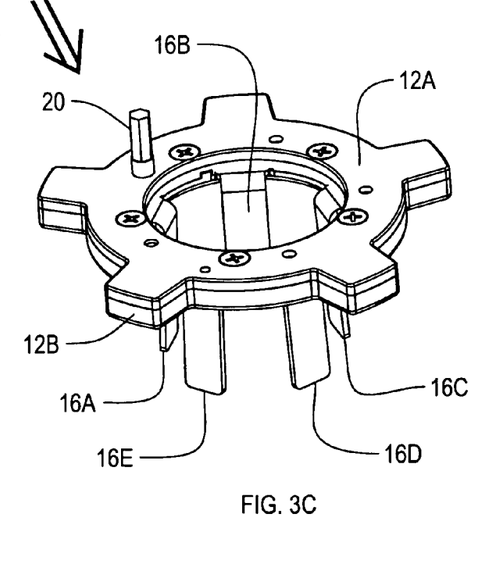

FIGS. 3A–3C illustrate the surgical retraction apparatus of FIG. 1 in its fully-retracted "open" configuration. FIG. 3B is a cross-sectional view across line B—B in FIG. 3A. In this configuration, the retraction arms 16A, 16B, 16C, 16D, 16E are radially disposed about the central axis 17 to form pieces of a broken tube-shaped structure as best shown in FIG. 2C. As is evident, the diameter of the broken-tube shaped structure formed by the retractor arms in the "open" configuration is significantly larger than the diameter of the tube-shaped structure formed by the retractor arms in the "closed" configuration.

Figure 4A:
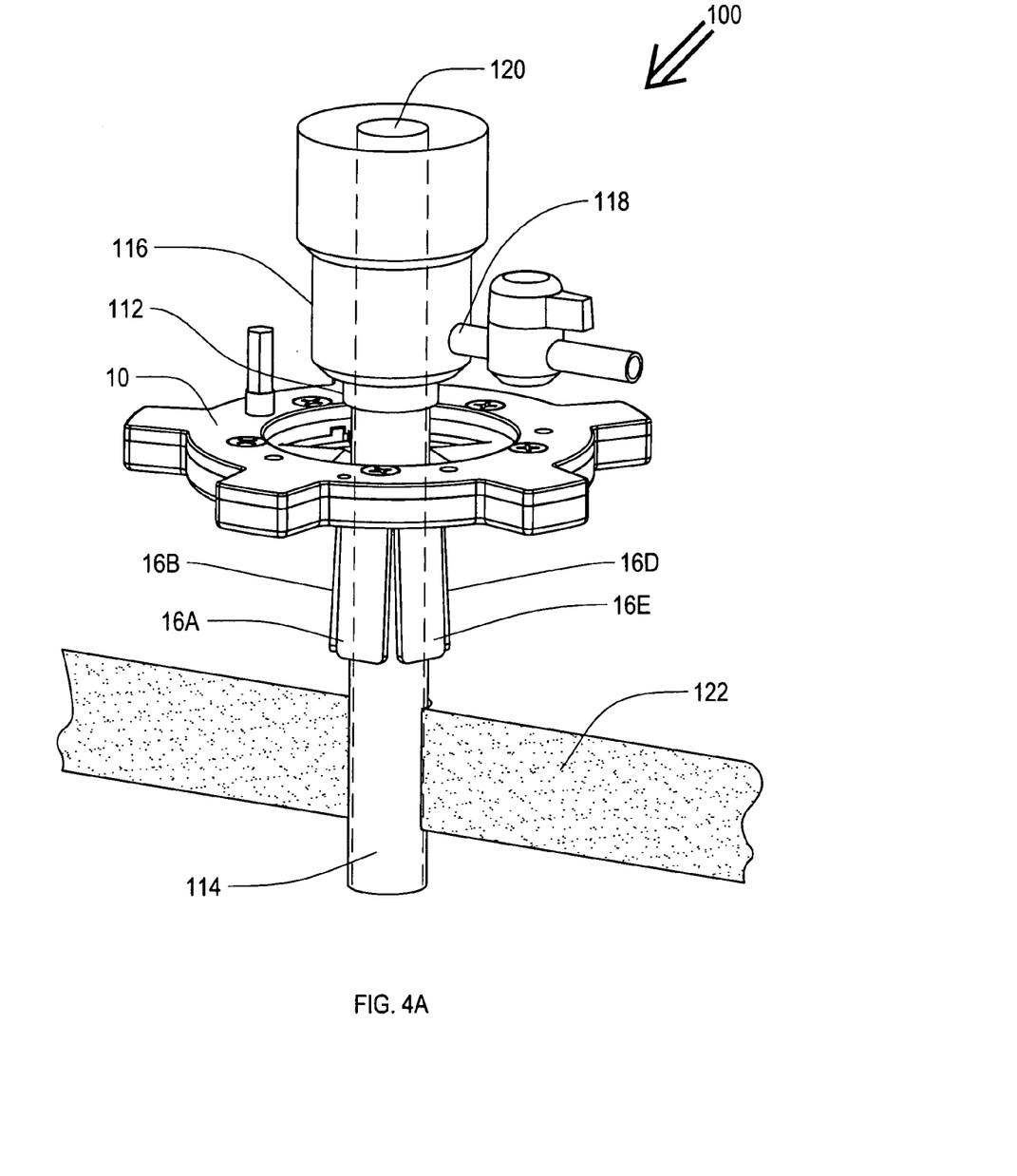
FIG. 4A is a view of the surgical retraction apparatus of FIG. 1 mounted onto the tubular section of a surgical port body that is inserted through the body wall of a patient during surgery.
Figure 4B:
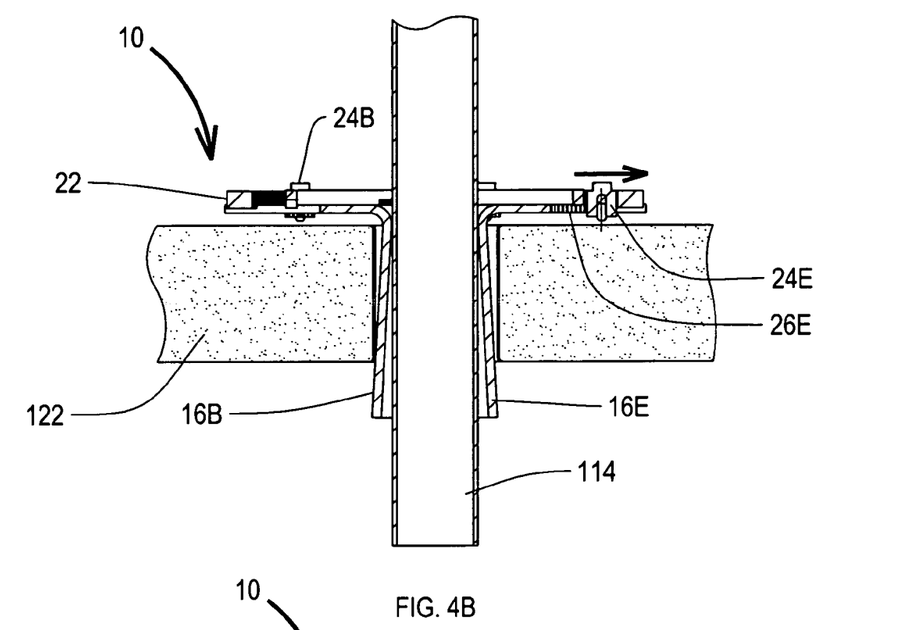
FIG. 4B is a diagrammatic view illustrating the insertion of the surgical retraction apparatus of FIG. 1 into regions between the tubular section of the port body and the body wall.
Figure 4C:
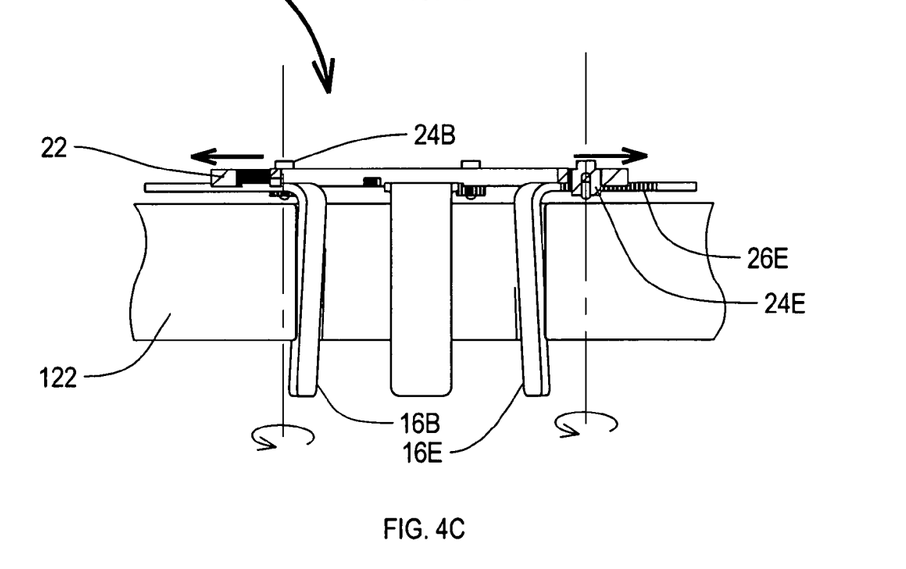
FIG. 4C is a diagrammatic view illustrating the retraction of the body wall by the retraction members of the surgical retraction apparatus of FIG. 1, with the port body removed from the large size opening created by such retraction.

Turning now to FIGS. 4A, 4B and 4C, there is shown an improved surgical port device 100 in accordance with the present invention, including a port body 112 with a rigid tubular section 114 and a side port section 116 disposed at the proximal end of the tubular section 114. The side port section 116 includes a side port 118 that is in fluid communication with a passageway 120 leading through the tubular section 114. The side port 118 is used for insufflation via an external pressure source operably coupled through the side port. In addition, the port body 112 includes a valve assembly (not shown) disposed at the proximal end of the port body 112 that maintains the elevated internal pressures in the body cavity during insufflation while inserting/removing instruments through the passageway 120 of the port body 112. The side port 118 may also be used for flushing as well. It should be appreciated that the side port section 116 may be omitted from the port body 112 while maintaining the valve assembly.

Figures 1A, 1B:
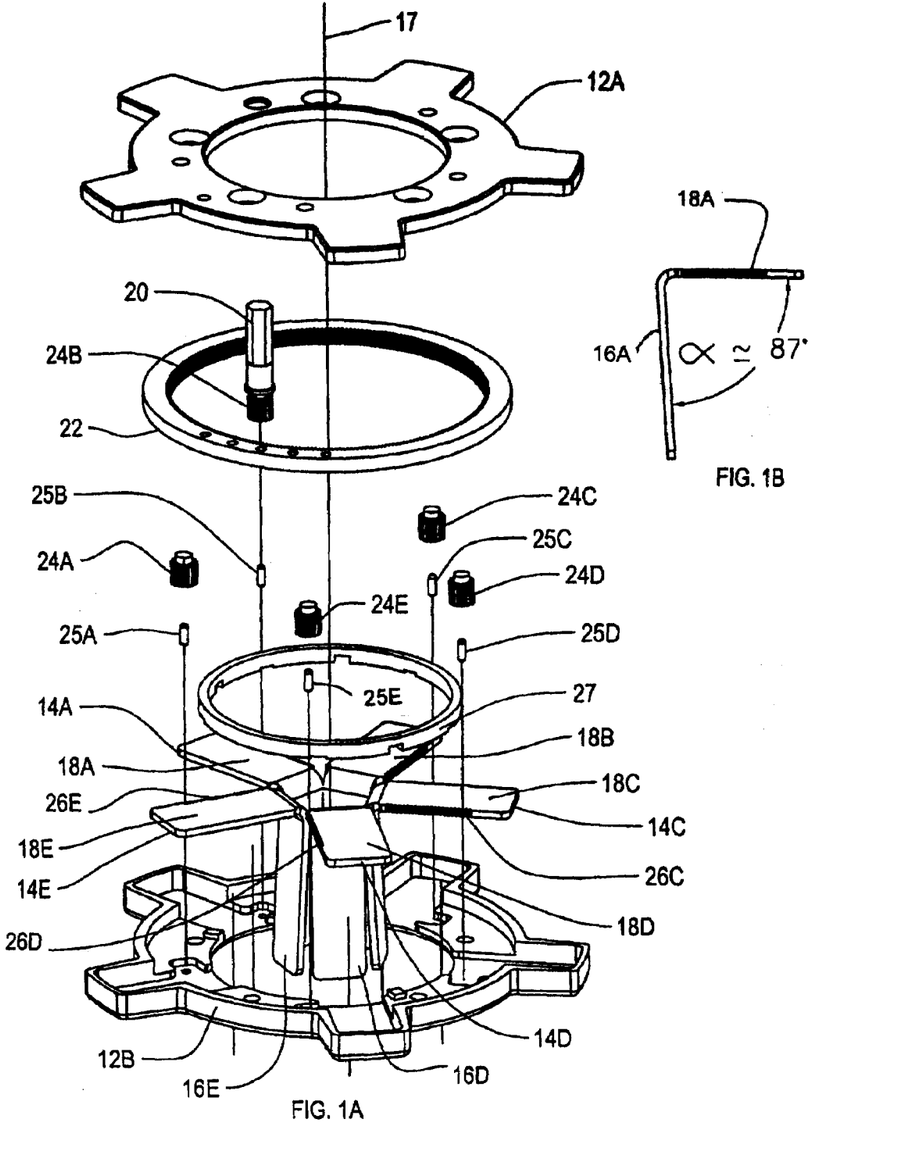
FIG. 1A is an exploded view of a surgical retraction apparatus in accordance with the present invention.
FIG. 1B is a partial side view of one of the retraction arms of FIG. 1A in accordance with the present invention.

The surgical retraction apparatus 10 of FIG. 1 is adapted such that the diameter of the tube shaped structure formed by the retractor arms in the "closed" configuration fits closely to the outer diameter surface of the tubular section 114. The surgical retraction device 10 is positioned in its "closed" configuration over the tubular section 114 as shown in FIG. 4A.

As described above, the port body 112 defines a passageway 120 through which surgical instruments are inserted and manipulated during surgical operations performed with the port device secured in place to the body wall. In order to secure the port device to the body wall of a patient, a sharp trocar assembly (which includes the port body) may be utilized to puncture the skin and body wall or an incision may be made into the skin at the desired entry site for the port device and an obturator (not shown) may be inserted into the passageway 120 of the port body 112 such that its tip extends from the distal end of the tubular section 114. The sharp trocar assembly (or the obturator and port body) are pushed through a narrow opening in the body wall at the entrance site. The sharp trocar assembly (or obturator) is then removed from the port body 112 such that tubular section 114 remains in the body wall 122 as shown in FIG. 4A.

After inserting the port body 112 through the body wall 122, irrigation of the entry site may be performed, if necessary. Surgical instruments (e.g., laparoscopic instruments, cutting blades, clamps/suturing devices, imaging probes, etc.) may then be inserted (and manipulated) into the body cavity through the passageway 120 provided by the port body 112 and the tubular section 114. During use, the orientation of the port body 112 may be manipulated such that it is angled with respect to the orientation of the narrow opening in the body wall at the entrance site. During such use, the body wall 122 exerts forces upon the port body 122. Preferably, the tubular section 114 is made of rigid material (for example, stainless steel, rigid plastic such as liquid crystal polymer or polycarbonate, glass-filled polycarbonate, or the like) such that the port body 112 does not substantially deform in response to such forces, thereby enabling the tubular structure of passageway 120 to substantially remain unchanged. In this manner, the orientation of the port body 112 may be angled via manipulation of the port body 112 without interfering with insertion, removal or other user manipulation of a medical instrument passing the passageway 120. This enables the medical instrument to freely move through the tubular section 114 while the orientation of the port body 112 is angled via manipulation.

When the tubular section 114 of the port device 100 is initially inserted into the body wall, the retraction apparatus 10 may be positioned such that the retraction arms 16A, 16B, 16C, 16D, 16E engage the body wall 122. Alternatively, it may be positioned proximal to the body wall 122, such that when retraction is desired, force is applied to the retraction apparatus 10 along the distal direction such that the retraction arms 16A, 16B, 16C, 16D, 16E engage the body wall 122. In either case, the retraction arms 16A, 16B, 16C, 16D, 16E are inserted into regions between the tubular section 114 and the body wall 122 as best shown in FIG. 4B. The user then rotates the handle or knob to retract the arms 16A, 16B, 16C, 16D, 16E in the radial direction away from the central axis 17 of the retraction apparatus as described above. The retraction of the retraction arms retracts the body wall 122 away from the tubular section 114 and increases the size opening into the body wall. The tubular section 114 (along with the port body 112) is then easily removed from the body wall 122 by lifting in the proximal direction, thereby leaving the large size opening in the body wall that is supported by the retraction arms of the retraction apparatus 10 as shown in FIG. 4C. Advantageously, the large size opening afforded by the retraction apparatus 10 enables the use of larger surgical instruments, enables visualization of the surgical site without a camera, and also enables the expeditious removal of larger organs (or pieces of such large organs) through the body wall 122.

With the port body 112 removed, the retractor apparatus 10 is preferably free-floating in the incision through the body wall. The retractor apparatus 10 may also be used in conjunction with a support apparatus (not shown) that retains the retractor apparatus 10 in a stationary position over the patient.

When retraction of the body wall 122 is no longer necessary, the user preferably rotates the handle or knob of the retractor apparatus 10 to retract the arms 16A, 16B, 16C, 16D, 16E in the radial direction towards the central axis (and preferably to its closed configuration as described above with respect to FIGS. 2A, 2B and 2C). The retraction apparatus 10 may be removed from the body wall 122 by applying a lifting force in the proximal direction. Alternatively, the tubular section 114 of the port body 112 may be re-inserted into the tubular-shaped structure formed by the arms 16A, 16B, 16C, 16D, 16E of the retraction apparatus 10 to continue the procedure using the port device. In any event, when the surgical procedure is finished, both the retraction apparatus 10 and the port body 112 are removed from the body wall 122 and the incision site is closed by conventional methods (such as stitching or stapling) or other desired methods.

Figure 5A:
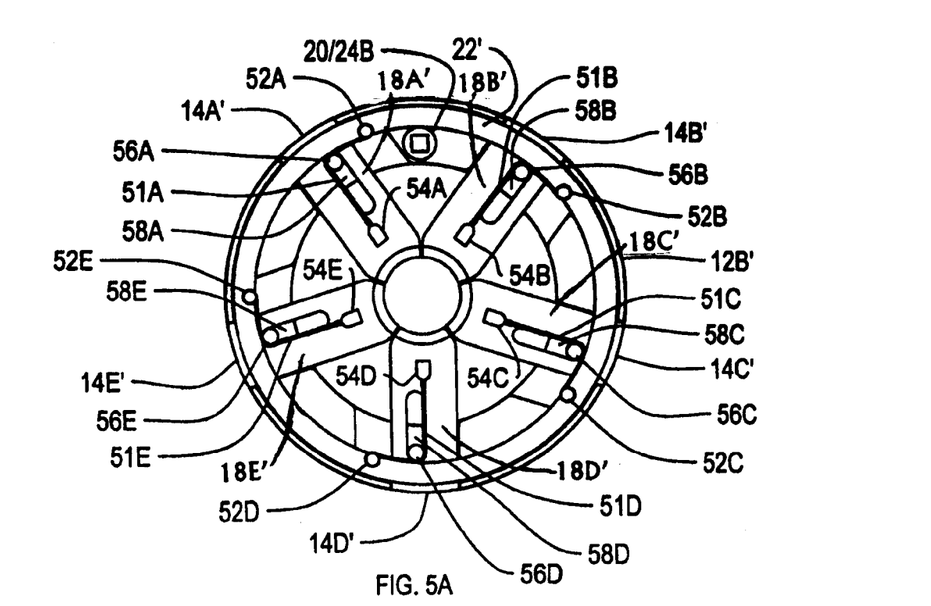
FIGS. 5A and 5B are schematic views illustrating an alternate embodiment of a surgical retraction apparatus according to the present invention wherein radial movement of the retraction members of the surgical retraction apparatus are effectuated with a cable and pulley mechanisms; the surgical retraction apparatus of FIG. 5A is in its non-retracted "closed" configuration; the surgical retraction apparatus of FIG. 5B is in its fully-retracted "open" configuration.
Figure 5B:
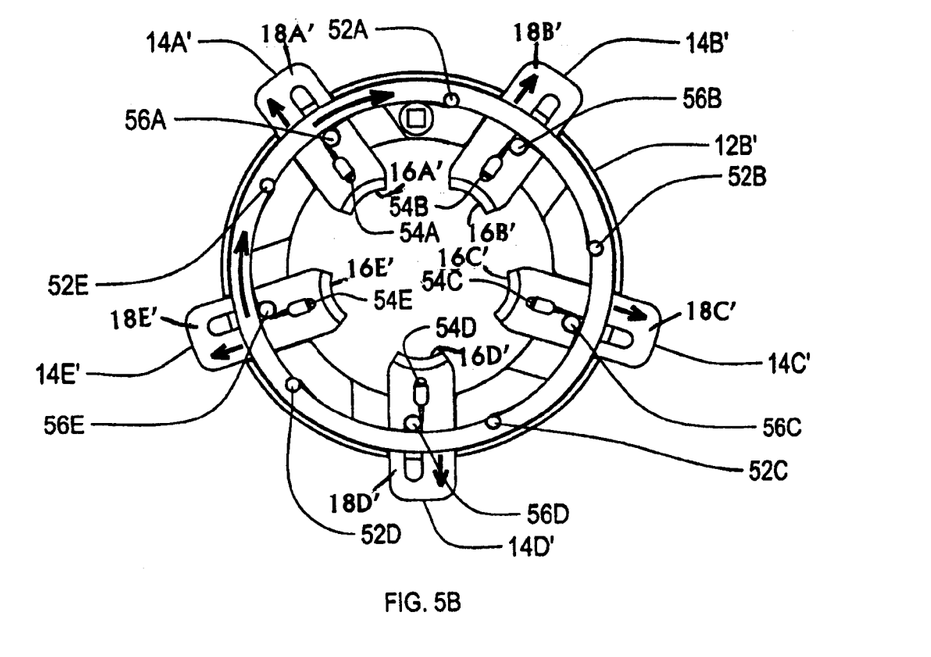

A second embodiment of a surgical retraction apparatus according to the present invention is shown in FIGS. 5A and 5B. In this second embodiment, the rack and pinion interfaces of the apparatus of FIGS. 1–3C are substituted with cable assemblies mounted within the housing (e.g., housing part 12B'). The cable assemblies are pulled around stationary posts to effectuate retraction of the retraction members. As shown, the cable assemblies include cables 51A, 51B, 51C, 51D, 51E whose ends are fixable attached to respective first connectors 52A, 52B, 52C, 52D, 52E and second connectors 54A, 54B, 54C, 54D, 54E. The first connectors 52A, 52B, 52C, 52D, 52E are mounted about the circumference of the sun gear 22', while the second connectors 54A, 54B, 54C, 54D, 54E are mounted to the segments 18A', 18B', 18C', 18D', 18E' of the retraction members 14A', 14B', 14C', 14D', 14E' preferably along a centerline of the segments as shown. Stationary posts (or pulleys) 56A, 56B, 56C, 56D, 56E are disposed in respective slots 58A, 58B, 58C, 58D, 58E in the segments 18A', 18B', 18C', 18D', 18E'. The cables 51A, 51B, 51C, 51D, 51E slide along the pulleys as the ring gear 22' is rotated in the clockwise-direction to thereby pull the segments 18A', 18B', 18C', 18D', 18E' and the corresponding retraction arms 16A', 16B', 16C', 16D', 16E' in the radial direction away from the central axis. The ring gear 22' is driven by rotation of a drive gear 24B and spline 20 in response to user rotation of a knob or arm attached to the spline 20 as described above. In this manner, user rotation of the knob or arm effectuates retraction of retraction arms 16A', 16B', 16C', 16D', 16E' in the radial direction away from the central axis. FIG. 5A illustrates the surgical retraction apparatus in its non-retracted "closed" configuration. In this configuration, the retraction arms form a substantially-closed tube-shaped structure about the central axis 17 similar to that shown in FIG. 2C. FIG. 5B illustrates the surgical retraction apparatus in its fully-retracted "open" configuration. In this configuration, the retraction arms are radially disposed about the central axis 17 to form pieces of a broken tube-shaped structure similar to that shown in FIG. 3C. As is evident, the diameter of the broken-tube shaped structure formed by the retractor arms in the "open" configuration is significantly larger than the diameter of the tube-shaped structure formed by the retractor arms in the "closed" configuration. The retraction arms may be moved radially toward the central axis (and retracted from the fully-retracted "open" position to the "closed" position) by manually applying force to the retraction arms to move them in this radial direction. Such movement pulls the cables 51A, 51B, 51C, 51D, 51E in the radial direction toward the central axis and causes the cables to slide along the stationary posts and rotate the ring gear 22' in the counter-clockwise direction to the "closed" configuration shown in FIG. 5A.

Figure 6A:
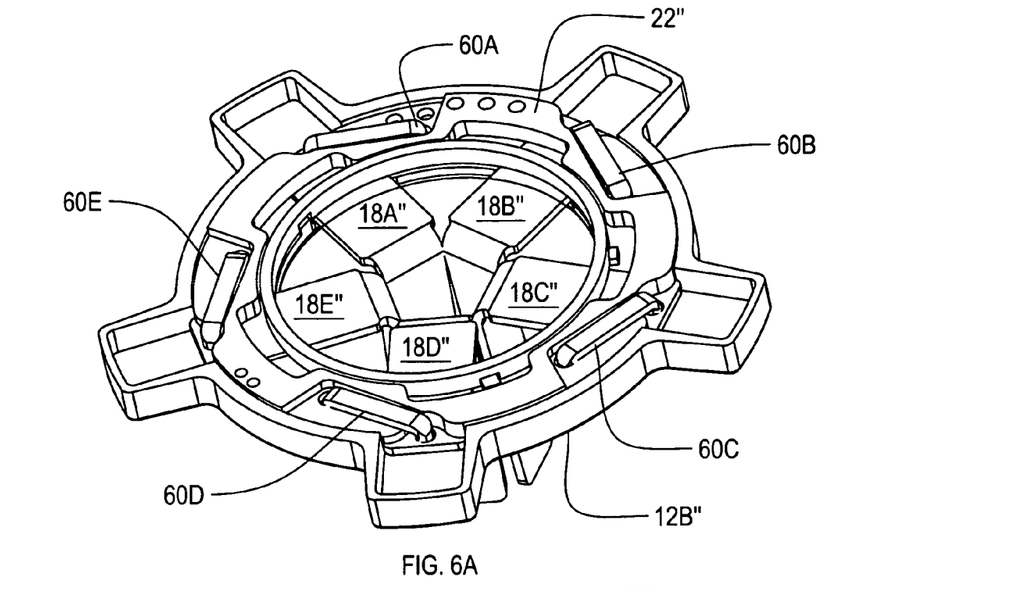
FIGS. 6A and 6B are isometric views illustrating an alternate embodiment of a surgical retraction apparatus according to the present invention wherein radial movement of the retraction members of the surgical retraction apparatus are effectuated with lever mechanisms; the surgical retraction apparatus of FIG. 6A is in its non-retracted "closed" configuration; the surgical retraction apparatus of FIG. 6B is in its fully-retracted "open" configuration.
Figure 6B:
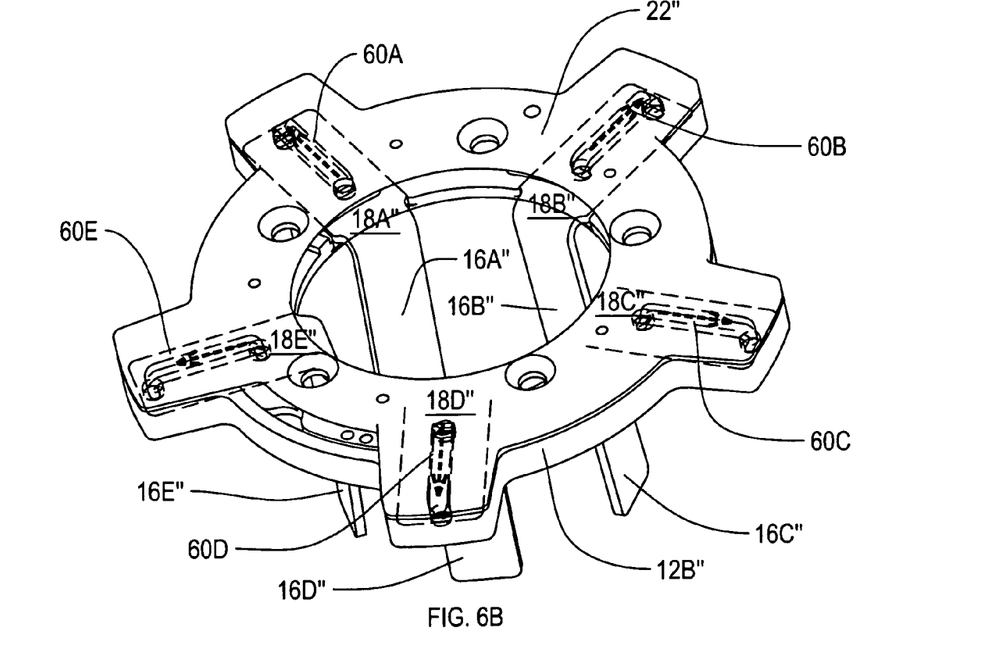

A third embodiment of a surgical retraction apparatus according to the present invention is shown in FIGS. 6A and 6B. In this third embodiment, the rack and pinion interfaces of the apparatus of FIGS. 1–3C are substituted with lever arms mounted within the housing (e.g., housing part 12B"). The lever arms effectuate retraction of the retraction members. As shown, the ends of lever arms 60A, 60B, 60C, 60D, 60E are mounted about the circumference of the sun gear 22" and about the segments 18A", 18B", 18C", 18D", 18E"

preferably along a centerline of the segments as shown. The lever arms 60A, 60B, 60C, 60D, 60E rotate as the ring gear 22" is rotated in the counter-clockwise-direction to thereby translate the segments 18A", 18B", 18C", 18D", 18E" and the corresponding retraction arms 16A", 16B", 16C", 16D", 16E" in the radial direction away from the central axis. Similarly, the lever arms 60A, 60B, 60C, 60D, 60E counter-rotate as the ring gear 22" is rotated in the clockwise-direction to thereby translate the segments 18A", 18B", 18C", 18D", 18E" and the corresponding retraction arms 16A", 16B", 16C", 16D", 16E" in the radial direction toward the central axis. The ring gear 22" is driven by rotation of a drive gear and spline in response to user rotation of a knob or arm attached to the spline as described above. In this manner, user rotation of the knob or arm effectuates retraction of retraction arms 16A", 16B", 16C", 16D", 16E" in the radial direction away from (and towards) the central axis. FIG. 6A illustrates the surgical retraction apparatus in its non-retracted "closed" configuration. In this configuration, the retraction arms form a substantially-closed tube-shaped structure about the central axis 17 similar to that shown in FIG. 2C. FIG. 6B illustrates the surgical retraction apparatus in its fully-retracted "open" configuration. In this configuration, the retraction arms are radially disposed about the central axis 17 to form pieces of a broken tube-shaped structure similar to that shown in FIG. 3C. As is evident, the diameter of the broken-tube shaped structure formed by the retractor arms in the "open" configuration is significantly larger than the diameter of the tube-shaped structure formed by the retractor arms in the "closed" configuration.

In the illustrative embodiments discussed above, the diameter of the broken-tube shaped structure formed by the retractor arms in the "open" configuration is approximately 40 mm, while the diameter of the tube shaped structure formed by the retractor arms in the "closed" configuration is approximately 12 mm (e.g., to closely accommodate a 10 mm trocar). Other open and closed diameters may be provided, as desired. Although, the provided structure is particularly advantageous in expanding by at least a factor of two or three.

In the illustrative embodiments discussed above, the retraction members are formed of a biocompatible rigid material (such as stainless steel, high strength metal alloys, high strength plastics or other materials) that provides sufficient strength to bear the loads placed thereon in use during retraction of the body wall. A flexible sleeve (not shown) may be disposed over the retraction arms so that the sleeve encircles the retraction arms. The sleeve forms a continuous surface between the arms that aids in preventing body tissue from entering into the tubular structure formed by the arms during retraction. The sleeve may be formed from a biocompatible latex, silicone elastomer, or a stainless steel cylindrical spring that slips pasts its own surface to provide varying diameter during retraction.

Figure 7A:
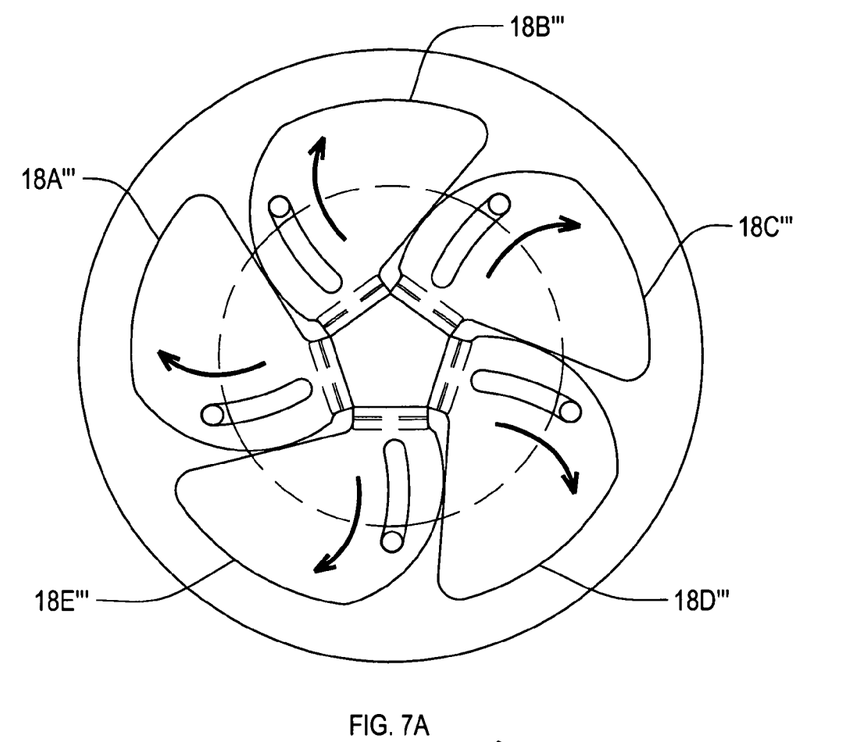
FIGS. 7A and 7B are diagrammatic views illustrating alternate embodiments of surgical retraction apparatus according to the present invention wherein the retraction members are nested about one another in the non-retracted "closed" configuration.
Figure 7B:
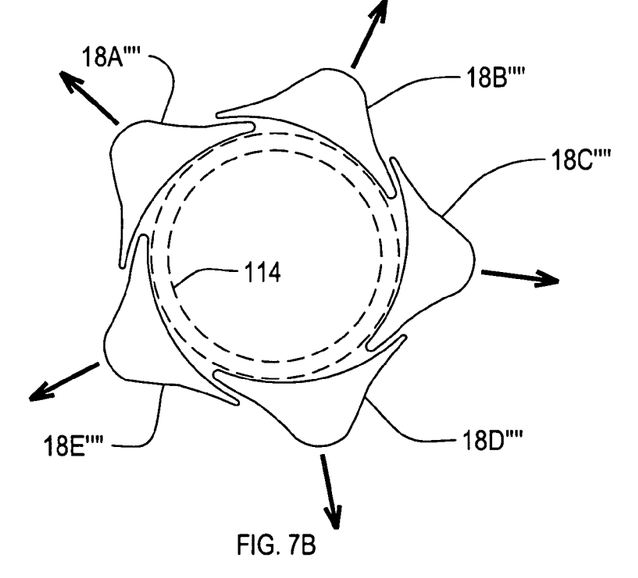

There have been described and illustrated herein an improved surgical retraction apparatus for use in conjunction with a surgical port device. Advantageously, the radial position of the retraction members of the surgical retraction apparatus are easily adjusted to provide a wide range of opening sizes into the body, and thus are effective in retracting the body wall over many different surgical applications. In addition, the surgical retraction apparatus of the present invention is simple to use and effective in conjunction with surgical port devices, and thus is effective in a wide range of laparoscopic and endoscopic procedures. While particular embodiments of the invention have been described, it is not intended that the invention be limited thereto, as it is intended that the invention be as broad in scope as the art will allow and that the specification be read likewise. Therefore, while the elements of the system have been particularly described with respect to their use with particular medical instruments, it may be used with other types of medical instruments. In addition, the surgical retraction apparatus and port devices described herein can be designed and manufactured with different sizes (e.g., varying length and cross-sectional diameter of the components), with different diameters, and with different materials. For example, closed diameters might range from 3 mm to 20 mm or larger, and open diameters might range from 10 mm to 50 mm or larger. Typically, the closed diameter will be between 10 mm and 20 mm and the open diameter will be between 30 mm and 50 mm. Moreover, it is contemplated that other mechanical drive designs, such as ratchet designs or adaptations of the designs described herein, can be used to control the radial retraction motion of the rigid retraction arms of the surgical retraction apparatus. It is also contemplated that the retraction members may be adapted to circumferentially mesh about one another in the closed configuration as shown in FIGS. 7A and 7B. In the configuration of FIG. 7A, the retraction arms are adapted to move relative to one another (e.g., slide, pivot) as well as move radially to effectuate retraction. In the configuration of FIG. 7B, the retraction arms overlap one another. This would enable the circumferential width of the retraction arms to be made larger to better prevent body tissue from entering into the tubular structure formed by the arms during retraction. It will therefore be appreciated by those skilled in the art that yet other modifications could be made to the provided invention without deviating from its spirit and scope as claimed.

What is claimed is:

1. A surgical retraction apparatus for use with a surgical port device having a tubular section that is inserted into tissue, the surgical retraction apparatus comprising:

at least three rigid retraction members disposed about a central axis; and a housing with guide slots corresponding to said retraction members, said guide slots directing movement of corresponding retraction members in substantially radical directions with respect to the central axis, said housing supporting a transmission assembly that imparts coordinated movement of said retraction members along the substantially radial directions between a closed state and an open state, wherein in said closed state said retraction members form a central opening that is adapted to closely fit around the tubular section of the surgical port device.

2. A surgical retraction apparatus according to claim 1, wherein:

said retraction members are L-shaped, each having an arm that projects along a direction substantially parallel to the central axis and a segment that projects along a directional substantially perpendicular to the central axis.

3. A surgical retraction apparatus according to claim 2, wherein:

the transmission assembly comprises a planetary gear train that impart the coordinated movement of said retraction members in the substantially radial directions.

4. A surgical retraction apparatus according to claim 3, wherein:

said planetary gear train comprises a drive gear, a sun gear that meshes to said drive gear, and a plurality of planetary pinion gears corresponding to said plurality of retraction members.

5. A surgical retraction apparatus according to claim 4, wherein:
the section of each retraction member comprises a rack surface that meshes to a corresponding planetary pinion gear to impart movement of the retraction member in its respective substantially radial direction in response to rotation of the drive gear and sun gear operably coupled thereto.

6. A surgical retraction apparatus according to claim 2, wherein:
the transmission assembly comprises a plurality of cables, operably coupled to said segments of said retraction members, that impart the coordinated movement of said retraction members in the substantially radial directions.

7. A surgical retraction apparatus according to claim 6, wherein:
each one of said plurality of cables, being operably coupled between a corresponding segment and a mounting element affixed to a rotating element, slides past a stationary post corresponding thereto.

8. A surgical retraction apparatus according to claim 2, wherein:
the transmission assembly comprises a plurality of lever arms, operably coupled to said segments of said retraction members, that controls impart he coordinated movement of said retraction members in the substantially radial directions.

9. A surgical retraction apparatus according to claim 8, wherein:
each one of said plurality of lever arms is operably coupled between a corresponding segment and a mounting element affixed to a rotating element.

10. A surgical retraction apparatus according to claim 2, wherein:
the segment of each retraction member is disposed with a respective guide slot.

11. A surgical retraction apparatus according to claim 1, wherein:
said retraction members form a tubular structure in the closed state that has a diameter in the range between 3 mm and 20 mm.

12. A surgical retraction apparatus according to claim 1, wherein:
said retraction members form a broken tubular structure in the open state that has a diameter in the range between 10 mm and 50 mm.

13. A surgical retraction apparatus according to claim 1, wherein:
said retraction members are formed from stainless steel.

14. A surgical retraction apparatus according to claim 1, wherein:
the transmission assembly comprises a roatable member housed within said housing and operably coupled to said retraction members, wherein said rotatable member is rotated to impart the coordinated movement of said retraction members in the substantially radial directions.

15. A surgical retraction apparatus according to claim 1, wherein:
said housing has an annular shape.

16. A surgical apparatus comprising:
a surgical port body having a tubular section that is inserted into tissue; and
a retraction subsystem having at least three rigid retraction members disposed about a central axis and a housing with guide slots corresponding to said retraction members, said guide slots directing movement of corresponding retraction members in substantially radial directions with respect to the central axis, said housing supporting a transmission assembly that imparts coordinated movement of said retraction members along the substantially radial directions between a closed state and an open state, wherein in said closed state said retraction members form a central opening that is adapted to closely fit around the tubular section of the surgical port body.

17. A surgical apparatus according to claim 16, wherein:
said transmission assembly comprises a planetary gear train that imparts the coordinated movement of said retraction members in the substantially radial directions.

18. A surgical apparatus according to claim 16, wherein:
said transmission assembly comprises a plurality of cables, operably coupled to said retraction members, that impart the corrdinated movement of said retraction members in the substantially radial directions.

19. A surgical apparatus according to claim 18, wherein:
each one of said plurality of cables, being operably coupled between a corresponding retraction member and a mounting element affixed to a rotating element, slides past a stationary post corresponding thereto.

20. A surgical apparatus according to claim 18, wherein:
each one of said plurality of lever arms is operably coupled between a corresponding retraction member and a mounting element affixed to a rotating element.

21. A surgical apparatus according to claim 16, wherein:
said transmission assembly comprises a plurality of lever arms, operably coupled to said retraction members, that impart the coordinated movement of said retraction members in the substantially radial directions.

22. A surgical apparatus according to claim 16, wherein:
said retraction members form a tubular structure in the closed state that has a diameter in the range between 3 mm and 20 mm.

23. A surgical apparatus according to claim 16, wherein:
said retraction members form a broken tubular structure in the open state that has a diameter in the range between 10 mm and 50 mm.

24. A surgical apparatus according to claim 16, wherein:
the transmission assembly comprises a rotatable member housed within said housing and operably coupled to said retraction members, wherein said rotatable member is rotated to impart the coordinated movement of said retraction members in the substantially radial directions.

25. A surgical apparatus according to claim 16, wherein:
said retraction members are L-shaped, each having an arm that projects along a direction substantially parallel to the central axis and a segment that projects along a directional substantially perpendicular to the central axis.

26. A surgical apparatus according to claim 25, wherein:
the segment of each retraction member is disposed within a respective guide slot.

27. A surgical apparatus according to claim 16, wherein:
said housing has an annular shape.

* * * * *